US010442986B2

(12) United States Patent
He et al.

(10) Patent No.: US 10,442,986 B2
(45) Date of Patent: Oct. 15, 2019

(54) DETERMINING RESIDUAL FRICTION REDUCER CONCENTRATIONS FOR SUBTERRANEAN TREATMENT FLUIDS

(71) Applicant: Multi-Chem Group, LLC, San Angelo, TX (US)

(72) Inventors: Kai He, Houston, TX (US); Liang Xu, The Woodlands, TX (US); Paul Lord, Cypress, TX (US)

(73) Assignee: Multi-Chem Group, LLC, Houston, TX (US)

( * ) Notice: Subject to any disclaimer, the term of this patent is extended or adjusted under 35 U.S.C. 154(b) by 0 days.

(21) Appl. No.: 16/090,410

(22) PCT Filed: May 31, 2016

(86) PCT No.: PCT/US2016/035061
§ 371 (c)(1),
(2) Date: Oct. 1, 2018

(87) PCT Pub. No.: WO2017/209740
PCT Pub. Date: Dec. 7, 2017

(65) Prior Publication Data
US 2019/0119563 A1  Apr. 25, 2019

(51) Int. Cl.
*E21B 43/267* (2006.01)
*E21B 43/26* (2006.01)
(Continued)

(52) U.S. Cl.
CPC ............. *C09K 8/68* (2013.01); *C09K 8/54* (2013.01); *C09K 8/602* (2013.01); *C09K 8/80* (2013.01);
(Continued)

(58) Field of Classification Search
CPC .... C09K 8/805; C09K 2208/28; C09K 8/536; C09K 2208/32; C09K 2208/12;
(Continued)

(56) References Cited

U.S. PATENT DOCUMENTS

2013/0196884 A1  8/2013  Kakadjian et al.
2015/0275627 A1  10/2015  Xu et al.
2015/0377010 A1  12/2015  Matherly et al.

FOREIGN PATENT DOCUMENTS

WO  88/00287 A1  1/1988

OTHER PUBLICATIONS

Allison, J. D., J. W. Wimberly, and T. L. Ely. "Automated and manual methods for the determination of polyacrylamide and other anionic polymers." SPE Reservoir Engineering 2.02 (1987): 184-188.
(Continued)

*Primary Examiner* — Zakiya W Bates
(74) *Attorney, Agent, or Firm* — Alan Bryson; Baker Botts L.L.P.

(57) ABSTRACT

Systems and methods for treating subterranean formations including quantifying additive concentrations. Certain of those methods include: introducing a fluid including an aqueous base fluid and a friction reducer into a wellbore penetrating of a subterranean formation at a pressure sufficient to create or enhance one or more fractures within the subterranean formation; recovering a portion of the fluid from the wellbore; adding a reactive agent to a sample of the portion of the fluid that has been recovered from the wellbore, where the reactive agent reacts with the friction reducer to form a photo-detectable compound in the sample; measuring a light absorbance of the sample at a selected wavelength of light; and using the measured absorbance and a calibration curve for the selected wavelength of light to
(Continued)

determine the concentration of the friction reducer in the fluid that has been recovered from the wellbore.

20 Claims, 4 Drawing Sheets

(51) Int. Cl.
| | | |
|---|---|---|
| *C09K 8/68* | (2006.01) | |
| *C09K 8/88* | (2006.01) | |
| *C09K 8/54* | (2006.01) | |
| *C09K 8/60* | (2006.01) | |
| *C09K 8/80* | (2006.01) | |
| *G01N 21/25* | (2006.01) | |

(52) U.S. Cl.
CPC .............. *C09K 8/882* (2013.01); *E21B 43/26* (2013.01); *E21B 43/267* (2013.01); *G01N 21/25* (2013.01); *C09K 2208/12* (2013.01); *C09K 2208/28* (2013.01); *C09K 2208/32* (2013.01)

(58) Field of Classification Search
CPC .... C09K 2208/20; C09K 8/524; C09K 8/605; E21B 43/267; E21B 37/00; E21B 43/26; E21B 43/11; E21B 43/119; E21B 43/34
See application file for complete search history.

(56) References Cited

OTHER PUBLICATIONS

Taylor, Kevin C. "Spectrophotometric determination of acrylamide polymers by flow injection analysis." SPE Advanced Technology Series 1.02 (1993): 130-133.

Chmilenko, F. A., I. V. Korobova, and S. V. Nazarenko. "Spectrophotometric determination of polyacrylamide in aqueous solutions using cationic dyes." Journal of Analytical Chemistry 59.2 (2004): 124-128.

Kuehne, D. L., and D. W. Shaw. "Manual and automated turbidimetric methods for the determination of polyacrylamides in the presence of sulfonates." Society of Petroleum Engineers Journal 25.05 (1985): 687-692.

International Search Report and Written Opinion issued in related PCT Application No. PCT/US2016/035061 dated Feb. 27, 2017, 11 pages.

DETERMINING RESIDUAL FRICTION REDUCER CONCENTRATIONS FOR SUBTERRANEAN TREATMENT FLUIDS

CROSS-REFERENCE TO RELATED APPLICATION

The present application is a U.S. National Stage Application of International Application No. PCT/US2016/035061 filed May 31, 2016, which is incorporated herein by reference in its entirety for all purposes.

BACKGROUND

The present disclosure relates to systems and methods for treating subterranean formations.

Treatment fluids may be used in a variety of subterranean treatments. Such treatments include, but are not limited to, stimulation treatments. As used herein, the term "treatment," or "treating," refers to any subterranean operation that uses a fluid in conjunction with a desired function and/or for a desired purpose. The term "treatment," or "treating," does not necessarily imply any particular action by the fluid.

One production stimulation operation that employs a treatment fluid is hydraulic fracturing. Hydraulic fracturing operations generally involve pumping a treatment fluid (e.g., a fracturing fluid) into a well bore that penetrates a subterranean formation at a sufficient hydraulic pressure to create or enhance one or more cracks, or "fractures," in the subterranean formation. The fracturing fluid may comprise particulates, often referred to as "proppant particulates," that are deposited in the fractures. The proppant particulates function, inter alia, to prevent the fractures from fully closing upon the release of hydraulic pressure, forming conductive channels through which fluids may flow to the well bore.

In certain approaches, hydraulic fracturing may use a cross-linked polymer to increase the viscosity of the fracturing fluid. The relatively high viscosity of such a fluid may, among other benefits, help transport the proppant particulates to the desired location within the formation and/or allow the fracturing fluid to be loaded with a higher concentration of proppant particulates. Once at least one fracture is created and the proppant particulates are substantially in place, the viscosity of the fracturing fluid usually is reduced, and the fracturing fluid may be recovered from the formation. The treatment fluid that is recovered is known as a flow-back fluid.

An alternative type of hydraulic fracturing, known as slickwater hydraulic fracturing, does not use a cross-linked polymer. The fracturing fluid has a relatively low viscosity as a result. Slickwater fracturing may be used to generate a narrow, complex fractures with low concentrations of proppants. Because the viscosity of the fracturing fluid is relatively low, the proppant transport is achieved by increasing the pumping rate and pressure of the fracturing fluid. During pumping, significant energy loss can occur due to the friction between the fracturing fluid and the casing or tubing, particularly when the fracturing fluid is in turbulent flow.

A friction reducer is often included in the fracturing fluid during slickwater fracturing operations to minimize such energy consumption. The friction reducer is typically a non-cross-linked polymer. It facilitates laminar flow of the treatment fluid, which causes less frictional forces and energy loss than turbulent flow of the same fluid. Due to the chemical nature of the friction reducer, however, the friction reducer can potentially damage the formation if it is not appropriately treated and breaks into low molecular weight fragments. Therefore, it can be advantageous to track the concentration of the friction reducer in the treatment fluid and particularly the flow-back fluid.

BRIEF DESCRIPTION OF THE DRAWINGS

These drawings illustrate certain aspects of some of the embodiments of the present disclosure, and should not be used to limit or define the claims.

Figure 1:
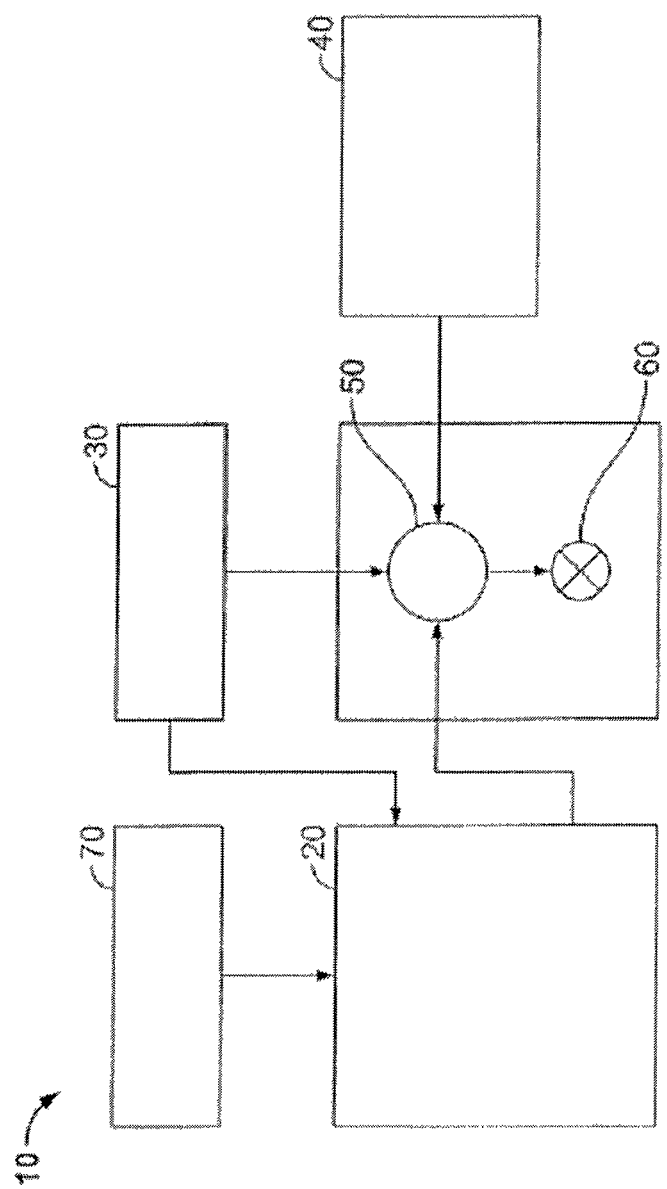
FIG. 1 is a diagram illustrating an example of a fracturing system that may be used in accordance with certain embodiments of the present disclosure.

While embodiments of this disclosure have been depicted, such embodiments do not imply a limitation on the disclosure, and no such limitation should be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DESCRIPTION OF CERTAIN EMBODIMENTS

The present disclosure relates to systems and methods for treating subterranean formations. More particularly, the present disclosure relates to systems and methods for quantifying the concentration of friction reducer in a flow-back fluid.

There may be several potential advantages to the methods and compositions of the present disclosure, only some of which are alluded to herein. The use of a friction reducer may be beneficial in treatment fluids, particularly because it can reduce energy loss that occurs due to the friction between the treatment fluid and the casing or tubing. However, the friction reducer can potentially cause damage to the formation if it is not appropriately treated. It is important to track the residual concentrations of the friction reducer in the treatment fluid that flows back, among other reasons, to determine whether a friction reducer breaker is required, for example, to prevent damage to the formation. The present disclosure provides a treatment fluid comprising a friction reducer and a spectrophotometric method to quantify the concentration of the friction reducer to provide a tool for tracking friction reducer residuals during the treatment of a well.

In accordance with embodiments of the present disclosure, a treatment fluid may comprise an aqueous base fluid and a friction reducer. The treatment fluid may comprise additional components, including but not limited to, proppants, acids (or salts thereof), surfactants, scale inhibitors, biocides, corrosion inhibitors, clay control, breakers, and any combination thereof. In certain embodiments, the treatment fluid may be used for slickwater hydraulic fracturing. However, the teachings of the present disclosure may be used in other treatments or subterranean fluids, including but not limited to, acidizing and drilling fluids.

The aqueous base fluid used in embodiments of the treatment fluids of the present disclosure may comprise fresh water, saltwater (e.g., water containing one or more salts dissolved therein), brine (e.g., saturated saltwater), seawater, or any combination thereof. Generally, the water may be from any source, provided that it does not contain components that might adversely affect the stability and/or performance of the treatment fluids of the present disclosure. One of ordinary skill in the art, with the benefit of this disclosure, will recognize what components might adversely affect the stability and/or performance of the treatment fluids of the present disclosure.

The friction reducer used in the treatment fluids of the present disclosure comprises one or more polymers that are not substantially cross-linked. In certain embodiments, the friction reducer comprises a polymeric chain without side chains. Examples of polymers that may be suitable include, but are not limited to, polyacrylamide, polyacrylamide derivatives, polyacrylamide co-polymers, and any combination thereof. In certain embodiments, the friction reducer has a molecular weight in the range of about 5,000 Daltons ("Da") to about 999,000,000 Da. In other embodiments, the friction reducer has a molecular weight in the range of about 1,000,000 Da to about 50,000,000 Da. In other embodiments, the friction reducer has a molecular weight in the range of about 3,000,000 Da to about 10,000,000 Da.

In some embodiments, the friction reducer may be present in a treatment fluid in an amount sufficient to maintain laminar flow when the treatment fluid is pumped into the well bore and/or subterranean formation. For example, in some embodiments, the friction reducer may be present in the treatment fluid in an amount of from about 100 to about 100,000 parts per million ("ppm"). In other example embodiments, the friction reducer may be present in the treatment fluid in an amount of from about 100 to about 5,000 ppm, or in other embodiments, from about 500 to about 2,000 ppm. In such embodiments, an amount of friction reducer on the higher end of the above ranges may be desired.

Without limiting the disclosure to any particular theory or mechanism, the friction reducer may decrease the energy loss that occurs when the treatment fluid is pumped at a high pumping rate or pressure. It is believed that the friction reducer helps maintain the laminar flow (as opposed to turbulent flow) of the treatment fluid. Laminar flow experiences reduced friction and, therefore, the treatment fluid suffers from less energy losses caused by this friction.

The treatment fluids of some embodiments may include particulates (such as proppant particulates or gravel particulates) suitable for use in subterranean applications. Particulates that may be suitable for use in certain embodiments of the present disclosure may comprise any material suitable for use in subterranean operations. Proppant particulates may be used in conjunction with hydraulic fracturing to prevent the fractures from fully closing upon the release of hydraulic pressure, forming conductive channels through which fluids may flow to the wellbore.

Particulate materials that may be suitable in certain embodiments include, but are not limited to, sand, bauxite, ceramic materials, glass materials, polymer materials, TEFLON® materials, nut shell pieces, cured resinous particulates comprising nut shell pieces, seed shell pieces, cured resinous particulates comprising seed shell pieces, fruit pit pieces, cured resinous particulates comprising fruit pit pieces, wood, composite particulates, and any combination thereof. Suitable composite particulates may comprise a binder and a filler material wherein suitable filler materials include silica, alumina, fumed carbon, carbon black, graphite, mica, titanium dioxide, meta-silicate, calcium silicate, kaolin, talc, zirconia, boron, fly ash, hollow glass microspheres, solid glass, and any combination thereof. The particulate size generally may range from about 2 mesh to about 400 mesh on the U.S. Sieve Series; however, in certain circumstances, other sizes may be desired and will be entirely suitable for practice of the present disclosures. In particular embodiments, preferred particulates size distribution ranges are one or more of 6/12, 8/16, 12/20, 16/30, 20/40, 30/50, 40/60, 40/70, or 50/70 mesh. It should be understood that the term "particulate," as used in this disclosure, includes all known shapes of materials, including substantially spherical materials, fibrous materials, polygonal materials (such as cubic materials), and mixtures thereof. Moreover, fibrous materials, that may or may not be used to bear the pressure of a closed fracture, are often included in fracturing and sand control treatments. In certain embodiments, the particulates included in the treatment fluids of some embodiments of the present disclosure may be coated with any suitable resin or tackifying agent known to those of ordinary skill in the art.

The treatment fluids of the present disclosure may be prepared by any suitable method. In some embodiments, the treatment fluids may be prepared on the job site. Furthermore, additional additives, as discussed above, may be combined with the treatment fluid and/or the aqueous base fluid as desired. For example, a particulate additive or particulates (e.g., gravel particulates or proppant particulates) may be suspended in the treatment fluid. One of ordinary skill in the art, with the benefit of this disclosure, will be able to determine other suitable methods for preparation of the treatment fluids.

The present disclosure also provides methods for using the treatment fluids to carry out a variety of subterranean treatments, including but not limited to, hydraulic fracturing treatments. In certain embodiments, a treatment fluid may be introduced into a subterranean formation. In some embodiments, the treatment fluid may be introduced into a well bore that penetrates a subterranean formation. In some embodiments, the treatment fluid may be introduced at a pressure sufficient to create or enhance one or more fractures within the subterranean formation (e.g., hydraulic fracturing). In some embodiments, the treatment fluid may flow back to the surface.

The present disclosure also provides a spectrophotometric method to quantify the concentration of friction reducer in a subject fluid. According to embodiments of the present disclosure, the spectrophotometric method comprises the steps of obtaining a sample of the subject fluid, preparing a calibration curve for the subject fluid using reference fluid samples based on the subject fluid, measuring a light absorbance of a sample of the subject fluid, and using the measured absorbance and the calibration curve to determine the concentration of the friction reducer in subject fluid.

The sample of the subject fluid may be obtained by any method known in the art. In certain embodiments, the subject fluid is a treatment fluid (e.g., a fracturing fluid). In certain embodiments, the subject fluid is a flow-back fluid. In some embodiments, the subject fluid is recovered from at least a portion of the fluid from the wellbore, for example, when the subject fluid is a flow-back fluid.

According to certain embodiments of the present disclosure, the preparation of the calibration curve comprises the steps of preparing reference fluid samples having a range of known concentrations of the friction reducer, treating the reference fluid samples with a reactive agent that reacts with the friction reducer to form a photo-detectable compound, measuring the light absorbance of each of the treated reference fluid samples, and fitting a trend-line to the light absorbance data.

The reference sample preparation begins with the preparation of a baseline fluid. The baseline fluid is prepared without friction reducer but is otherwise designed to approximate the characteristics of the subject fluid. In certain embodiments, the baseline fluid has the same density, pH, salinity, and/or type of salts and ions as the subject fluid. These characteristics may be measured using any technique known in the art. For example, mass spectrometry or other analytical techniques may be used to determine the concentration of ions in the subject fluid. The characteristics of the subject fluid may also be determined based on known attributes of the well bore or subterranean formation. Known quantities of friction reducer may be added to known quantities of the baseline fluid to produce reference samples having known concentrations of friction reducer. A plurality of reference samples are prepared having a range of known concentrations of friction reducer. In certain embodiments, the known concentrations of friction reducer in the reference samples range from about 0.01 ppm to about 1,000 ppm.

The reference samples are then treated with one or more reactive agents. Without limiting the disclosure to any particular theory or mechanism, the reactive agent reacts with the friction reducer in the sample to produce a photo-detectable compound that affects the light absorbance of the sample. In some embodiments, the photo-detectable compound is a precipitate. In certain embodiments, the amount of photo-detectable compound is proportional to the concentration of the friction reducer. Suitable reactive agents include any compound that can be used to form a photo-detectable compound when it is added to a solution having the friction reducer. In certain embodiments, the photo-detectable compound is a complex of the friction reducer and/or the reactive agent. In other embodiments, the reaction of the friction reducer and the reactive agent produces intermediate compounds that may be involved in subsequent reactions that produce a photo-detectable compound. In some embodiments, a cationic dye may be used to precipitate an anionic friction reducer. In other embodiments, an anionic dye may be used to precipitate a cationic friction reducer. One example of a reactive agent that may be suitable in certain embodiments of the present disclosure is HYAMINE® 1622 (Diisobutylphenoxyethoxyethyl)dimethylbenzylammonium chloride solution, available from Sigma-Aldrich). Another reactive agent that may be suitable in certain embodiments of the present disclosure is Methylene Blue, which in certain embodiments may be used to precipitate an anionic friction reducer such as polyacrylamide.

In certain alternative embodiments, and depending on the friction reducer, iodide may be oxidized to iodine to form a photo-detectable compound comprising "starch-triiodide" complex. In these embodiments, an excess of $Br_2$ is added to the fluid containing a friction reducer (such as polyacrylamide) where it reacts to form an N-bromo amide. This N-bromo amide subsequently reacts with water in the fluid to form hypobromous acid. An excess of hydroiodic acid is then added and it reacts with the hypobromous acid to form $I_2$ (with hydrobromic acid and water byproducts). Starch is added to the fluid and forms a starch-triiodide complex with the $I_2$ and $I^-$. The amount of starch-triiodide depends on the original concentration of the friction reducer.

In some embodiments, the reference samples may be treated with a masking agent before they are treated with the reactive agent. Without limiting the disclosure to any particular theory or mechanism, the masking agent may substantially prevent the precipitation of components in the subject fluid other than the friction reducing agent. One example of a masking agent that may be suitable in certain embodiments of the present disclosure is sodium citrate. Another example of a masking agent that may be suitable in certain embodiments of the present disclosure is butanol. In certain embodiments, the masking agent may be added to the reference sample in a concentration from about 0.01% to about 10% by weight.

The light absorbance of each of the reference samples is then measured. Without being limited by theory, it is believed that the light absorbance of the sample depends on the concentration of photo-detectable compound present in the sample. In certain embodiments, each of the reference samples are tested separately in an ultraviolet-visible (UV-Vis) spectrophotometer. An example of a UV-Vis spectrophotometer that may be suitable for use in the methods of the present disclosure is a V-660 spectrophotometer available from Jasco. Each reference sample is exposed to a range of wavelengths of light and the absorbance is measured at intervals over range of the wavelengths. In some embodiments, the reference samples are measured at wavelengths from about 190 nm to about 900 nm. In some embodiments, absorption measurements are taken at every 0.5 nm in the selected range of wavelengths. However, in other embodiments, the absorption measurements may be taken at different intervals that are more frequent or less frequent.

A calibration curve is prepared for the subject fluid at a selected wavelength using the light absorbance data of the reference samples described above. The wavelength of light that results in the peak absorbance (i.e., the peak wavelength) is determined. Then, for each reference sample that was tested, the absorbance at the peak wavelength is plotted against the concentration of friction reducer in that reference sample. A trend-line is then fit to the data. In certain embodiments, the trend-line is linear. The trend-line can be used to determine the concentration of friction reducer as a function of the absorbance at the peak wavelength of a sample of another fluid.

The calibration curve may then be used to determine the concentration of the friction reducer in the subject fluid. A sample of the subject fluid is treated with the same reactive agent or reactive agents as the reference samples in the preparation of the calibration curve as described above. If the reference samples had been optionally treated with a masking agent, then the sample of the subject fluid is treated with the same masking agent. The light absorbance of the subject fluid is then measured at the selected wavelength. By comparing the light absorbance to the calibration curve, the concentration of friction reducer can be determined.

In some embodiments, the method of the present disclosure may be used to track the friction reducer used in slickwater fracturing. A treatment fluid comprising a friction reducer may be introduced into a wellbore according to the teachings of the present disclosure, and a portion of that fluid may be subsequently recovered from the wellbore. A calibration curve for the flow-back fluid may be prepared according to the teachings of the present disclosure. The concentration of friction reducer in the flow-back fluid may be determined by treating a sample of the flow-back fluid with the reactive agent, measuring the light absorption of the sample, and comparing the absorbance to the calibration curve. By comparing the concentration of the friction reducer in the flow-back fluid to the concentration of the friction reducer in the treatment fluid, one can determine whether the friction reducer is being lost to the formation.

The methods and compositions disclosed herein may directly or indirectly affect one or more components or pieces of equipment associated with the preparation, delivery, recapture, recycling, reuse, and/or disposal of the disclosed compositions. For example, and with reference to FIG. 1, the disclosed methods and compositions may directly or indirectly affect one or more components or pieces of equipment associated with an exemplary fracturing system 10, according to one or more embodiments. In certain instances, the system 10 includes a fracturing fluid producing apparatus 20, a fluid source 30, a proppant source 40, and a pump and blender system 50 and resides at the surface at a well site where a well 60 is located. In certain instances, the fracturing fluid producing apparatus 20 combines a pre-cursor with fluid (e.g., liquid or substantially liquid) from fluid source 30, to produce a hydrated fracturing fluid that is used to fracture the formation. The hydrated fracturing fluid can be a fluid for ready use in a fracture stimulation treatment of the well 60 or a concentrate to which additional fluid is added prior to use in a fracture stimulation of the well 60. In other instances, the fracturing fluid producing apparatus 20 can be omitted and the fracturing fluid sourced directly from the fluid source 30.

The proppant source 40 can include a proppant for combination with the fracturing fluid. The system may also include additive source 70 that provides one or more additives (e.g., friction reducers, weighting agents, and/or other optional additives) to alter the properties of the fracturing fluid. For example, the other additives 70 can be included to reduce pumping friction, to reduce or eliminate the fluid's reaction to the geological formation in which the well is formed, to operate as surfactants, and/or to serve other functions.

The pump and blender system 50 receives the fracturing fluid and combines it with other components, including proppant from the proppant source 40 and/or additional fluid from the additives 70. The resulting mixture may be pumped down the well 60 under a pressure sufficient to create or enhance one or more fractures in a subterranean zone, for example, to stimulate production of fluids from the zone. Notably, in certain instances, the fracturing fluid producing apparatus 20, fluid source 30, and/or proppant source 40 may be equipped with one or more metering devices (not shown) to control the flow of fluids, proppants, and/or other compositions to the pumping and blender system 50. Such metering devices may permit the pumping and blender system 50 can source from one, some or all of the different sources at a given time, and may facilitate the preparation of fracturing fluids in accordance with the present disclosure using continuous mixing or "on-the-fly" methods. Thus, for example, the pumping and blender system 50 can provide just fracturing fluid into the well at some times, just proppants at other times, and combinations of those components at yet other times.

Figure 2:
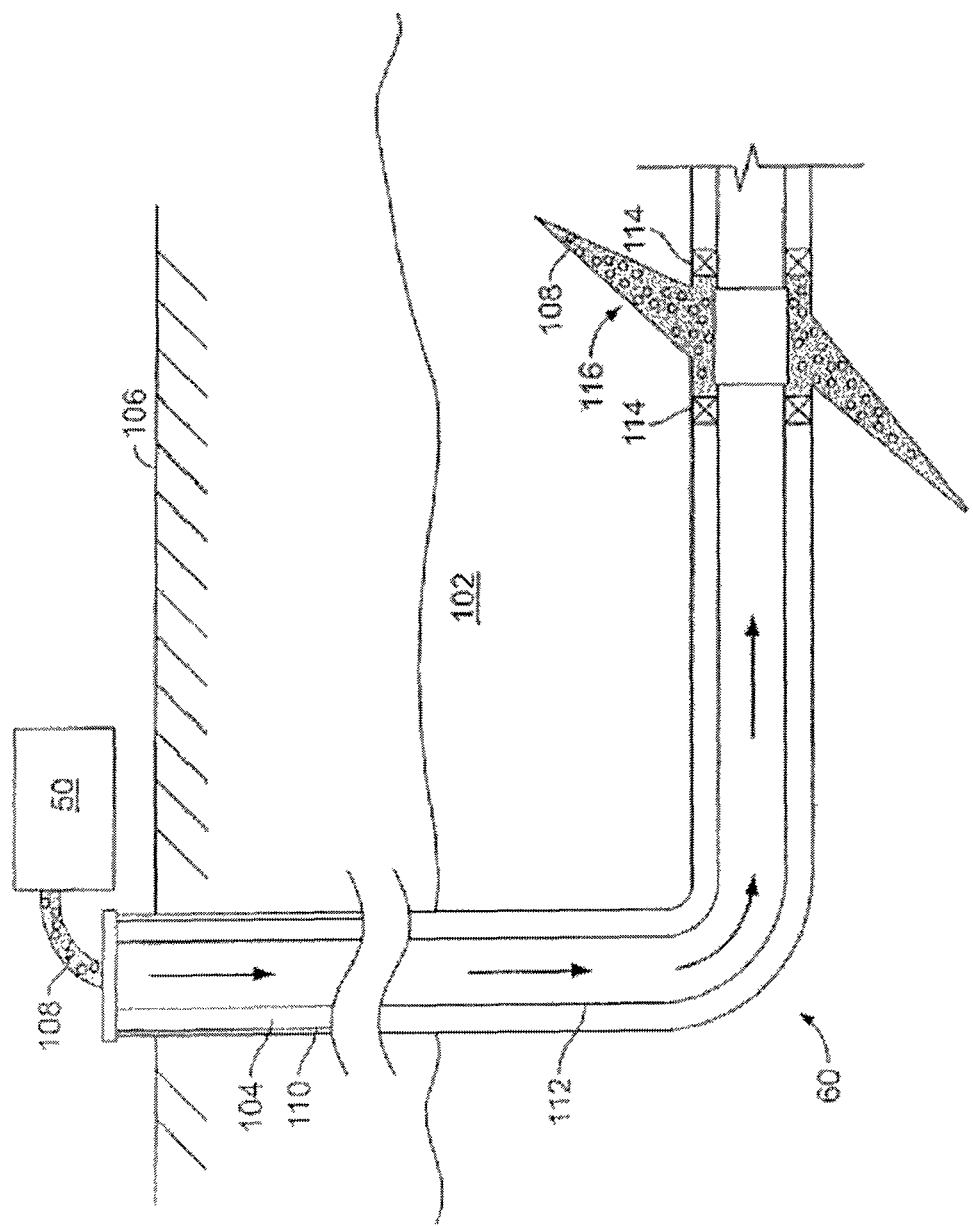
FIG. 2 is a diagram illustrating an example of a subterranean formation in which a fracturing operation may be performed in accordance with certain embodiments of the present disclosure.

FIG. 2 shows the well 60 during a fracturing operation in a portion of a subterranean formation of interest 102 surrounding a well bore 104. The well bore 104 extends from the surface 106, and the fracturing fluid 108 is applied to a portion of the subterranean formation 102 surrounding the horizontal portion of the well bore. Although shown as vertical deviating to horizontal, the well bore 104 may include horizontal, vertical, slant, curved, and other types of well bore geometries and orientations, and the fracturing treatment may be applied to a subterranean zone surrounding any portion of the well bore. The well bore 104 can include a casing 110 that is cemented or otherwise secured to the well bore wall. The well bore 104 can be uncased or include uncased sections. Perforations can be formed in the casing 110 to allow fracturing fluids and/or other materials to flow into the subterranean formation 102. In cased wells, perforations can be formed using shape charges, a perforating gun, hydro-jetting and/or other tools.

The well is shown with a work string 112 depending from the surface 106 into the well bore 104. The pump and blender system 50 is coupled a work string 112 to pump the fracturing fluid 108 into the well bore 104. The working string 112 may include coiled tubing, jointed pipe, and/or other structures that allow fluid to flow into the well bore 104. The working string 112 can include flow control devices, bypass valves, ports, and or other tools or well devices that control a flow of fluid from the interior of the working string 112 into the subterranean zone 102. For example, the working string 112 may include ports adjacent the well bore wall to communicate the fracturing fluid 108 directly into the subterranean formation 102, and/or the working string 112 may include ports that are spaced apart from the well bore wall to communicate the fracturing fluid 108 into an annulus in the well bore between the working string 112 and the well bore wall.

The working string 112 and/or the well bore 104 may include one or more sets of packers 114 that seal the annulus between the working string 112 and well bore 104 to define an interval of the well bore 104 into which the fracturing fluid 108 will be pumped. FIG. 2 shows two packers 114, one defining an uphole boundary of the interval and one defining the downhole end of the interval. When the fracturing fluid 108 is introduced into well bore 104 (e.g., in FIG. 2, the area of the well bore 104 between packers 114) at a sufficient hydraulic pressure, one or more fractures 116 may be created in the subterranean zone 102. The proppant particulates in the fracturing fluid 108 may enter the fractures 116 where they may remain after the fracturing fluid flows out of the well bore. These proppant particulates may "prop" fractures 116 such that fluids may flow more freely through the fractures 116.

While not specifically illustrated herein, the disclosed methods and compositions may also directly or indirectly affect any transport or delivery equipment used to convey the compositions to the fracturing system 10 such as, for example, any transport vessels, conduits, pipelines, trucks, tubulars, and/or pipes used to fluidically move the compositions from one location to another, any pumps, compressors, or motors used to drive the compositions into motion, any valves or related joints used to regulate the pressure or flow rate of the compositions, and any sensors (i.e., pressure and temperature), gauges, and/or combinations thereof, and the like.

EXAMPLES

To facilitate a better understanding of the present disclosure, the following examples of certain aspects of some embodiments are given. In no way should the following examples be read to limit or define the scope of the claims.

Example 1

The following steps illustrate the preparation of a calibration curve for a friction reducer. First, a series of 30 mL reference samples were prepared as shown in Table 1 below. A baseline reference sample with no friction reducer and then reference samples containing a concentration of friction reducer (up to 1000 ppm) were mixed with 10 ml of 5% sodium citrate and 10 ml of 4 mM HYAMINE® 1622 solution. The reference samples were allowed to rest for 30 minutes. As the concentration of friction reducer increases, the reference samples appear cloudier due to increased precipitation.

Figure 3:
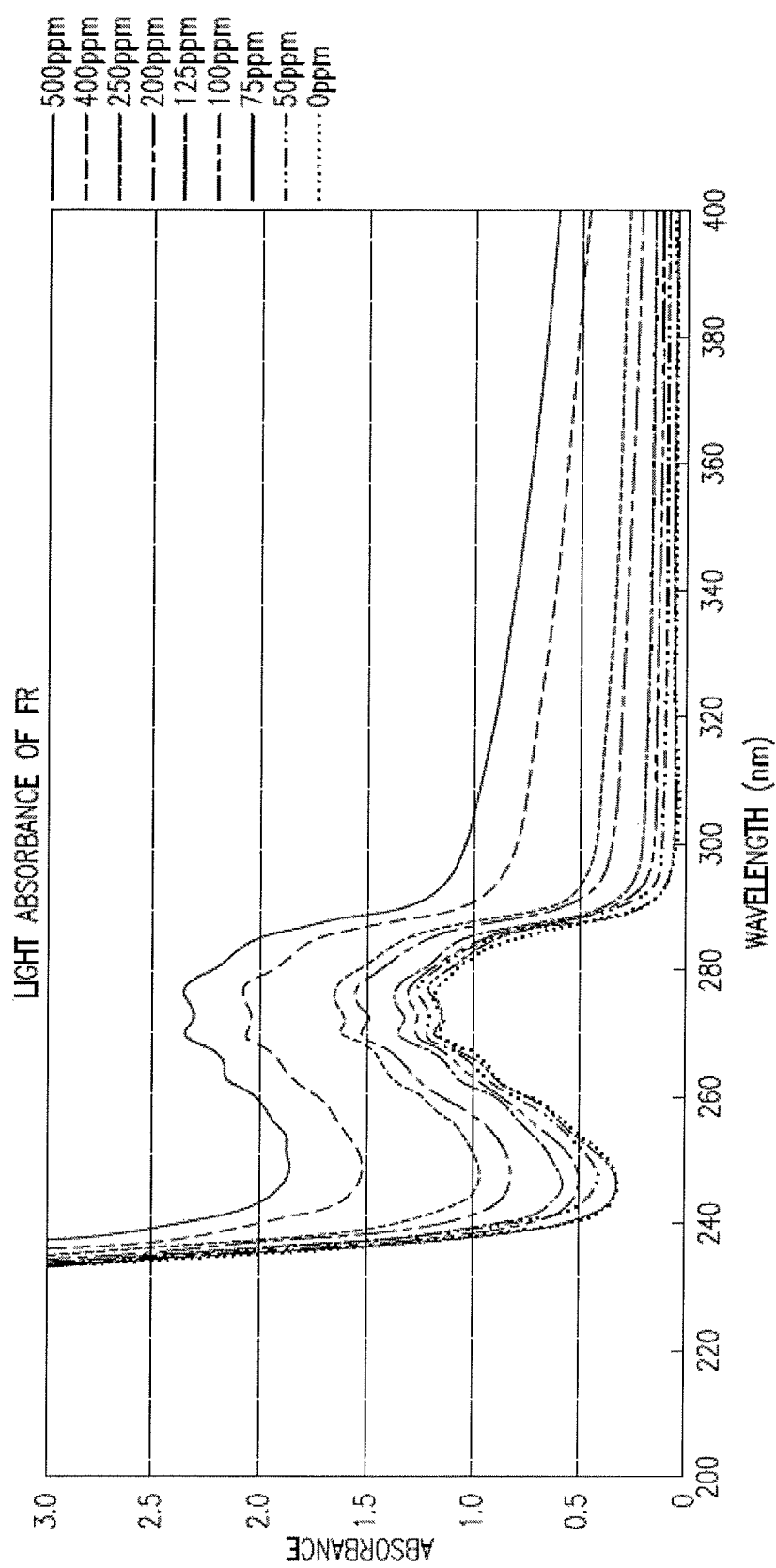
FIG. 3 is a graph that illustrates light absorbance of samples that were measured in accordance with certain embodiments of the present disclosure.

After 30 minutes, the reference samples were placed in an ultraviolet-visible (UV-Vis) spectrophotometer to measure the light absorbance over a range of wavelengths. FIG. 3 illustrates the light absorbance of each sample as a function of the wavelength of the light for a subset of the samples (0, 50, 75, 100, 125, 200, 250, 400 and 500 ppm). A peak absorbance can be observed at 276.5 nm.

Figure 4:
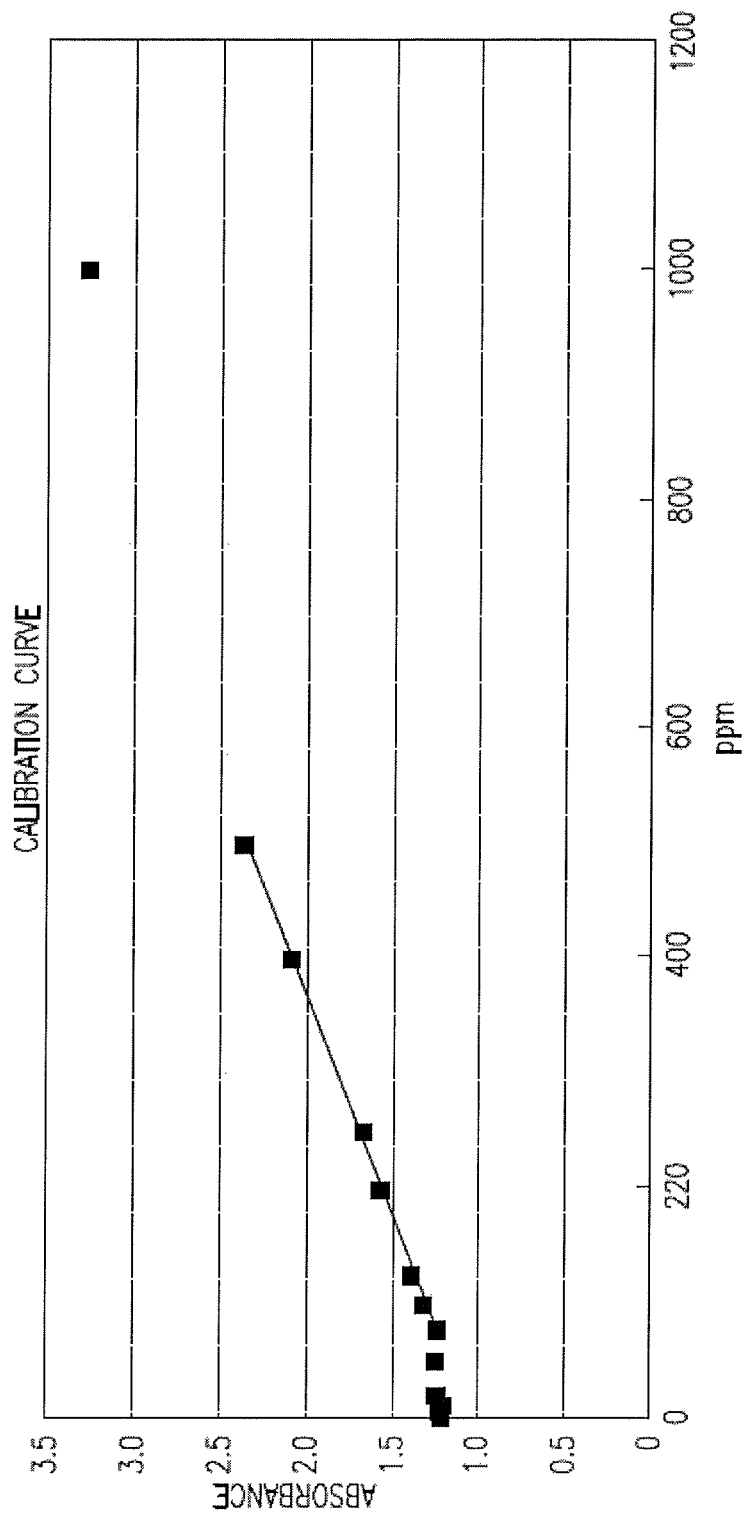
FIG. 4 is a calibration curve that was prepared in accordance with certain embodiments of the present disclosure.

Finally, a calibration curve was prepared using the absorbance results at 276.5 nm for all of the reference samples. The calibration curve was prepared using the reference samples shown in FIG. 3 as well as four additional concentrations (5, 10, 20, 1000 ppm). For each sample, the concentration of friction reducer (X-axis) was plotted against the absorbance measured at 276.5 nm (Y-axis). FIG. 4 illustrates this calibration curve which shows the absorbance as a function of the concentration of friction reducer. The curve is linear from 75 ppm to 500 ppm for the tested friction reducer:

$$Y=0.0026*X+1.0407$$

$$R^2=0.9985 \quad [\text{Eq. 1}]$$

where Y is the Absorbance and X is the Concentration of friction reducer. Using this constructed calibration curve and equation, an unknown concentration of friction reducer in a sample can be calculated from the absorbance at 276.5 nm of the sample.

An embodiment of the present disclosure is a method comprising: introducing a fluid comprising an aqueous base fluid and a friction reducer into a wellbore penetrating at least a portion of a subterranean formation at a pressure sufficient to create or enhance one or more fractures within the subterranean formation; recovering at least a portion of the fluid from the wellbore; adding a reactive agent to a sample of the portion of the fluid that has been recovered from the wellbore, wherein the reactive agent reacts with the friction reducer to form a photo-detectable compound in the sample; measuring a light absorbance of the sample of the fluid that has been recovered from the wellbore at a selected wavelength of light; and using the measured absorbance and a calibration curve for the selected wavelength of light to determine the concentration of the friction reducer in the fluid that has been recovered from the wellbore. Optionally, the method further comprises the step of preparing the calibration curve, wherein the preparation of the calibration curve comprises: preparing a plurality of reference fluid samples having a range of known concentrations of the friction reducer, treating the reference fluid samples with the reactive agent, measuring the light absorbance of each of the treated reference fluid samples, and fitting a trend-line to the light absorbance data. Optionally, the reactive agent comprises diisobutylphenoxyethoxyethyl dimethylbenzylammonium chloride. Optionally, the method further comprises adding a masking agent comprising sodium citrate to the sample before the reactive agent is added to the sample. Optionally, the photo-detectable compound is a precipitate. Optionally, the friction reducer comprises polyacrylamide. Optionally, the fluid further comprises an additive selected from the group of additives consisting of a surfactant, a proppant particle, a corrosion inhibitor, a clay stabilizer, and any combination thereof. Optionally, the fluid is injected into the wellbore using one or more pumps.

Another embodiment of the present disclosure is a method comprising: introducing a fluid comprising an aqueous base fluid and a friction reducer comprising polyacrylamide into a wellbore penetrating at least a portion of a subterranean formation; recovering at least a portion of the fluid from the wellbore; adding a reactive agent comprising diisobutylphenoxyethoxyethyl dimethylbenzylammonium chloride to a sample of the portion of the fluid that has been recovered from the wellbore, wherein the reactive agent reacts with the friction reducer to form a photo-detectable compound in the sample; measuring a light absorbance of the sample of the fluid that has been recovered from the wellbore at a selected wavelength of light; and using the measured absorbance and a calibration curve for the selected wavelength of light to determine the concentration of the friction reducer in the fluid that has been recovered from the wellbore. Optionally, the method further comprises the step of preparing the calibration curve, wherein the preparation of the calibration curve comprises: preparing a plurality of reference fluid samples having a range of known concentrations of the friction reducer, treating the reference fluid samples with the reactive agent, measuring the light absorbance of each of the treated reference fluid samples, and fitting a trend-line to the light absorbance data. Optionally, the method further comprises adding a masking agent comprising sodium citrate to the sample before the reactive agent is added to the sample. Optionally, the photo-detectable compound is a precipitate. Optionally, the fluid further comprises an additive selected from the group of additives consisting of a surfactant, a proppant particle, a corrosion inhibitor, a clay stabilizer, and any combination thereof Optionally, the fluid is injected using one or more pumps. Optionally, the fluid is injected into the wellbore at a pressure sufficient to create or enhance one or more fractures within the subterranean formation.

Another embodiment of the present disclosure is a method comprising: introducing a fluid comprising an aqueous base fluid and a friction reducer comprising polyacrylamide into a wellbore penetrating at least a portion of a subterranean formation at a pressure sufficient to create or enhance one or more fractures within the subterranean formation; recovering at least a portion of the fluid from the wellbore; adding a reactive agent comprising diisobutylphenoxyethoxyethyl dimethylbenzylammonium chloride solution to a sample of the portion of the fluid that has been recovered from the wellbore, wherein the reactive agent reacts with the friction reducer to form a photo-detectable compound in the sample; measuring a light absorbance of the sample of the fluid that has been recovered from the wellbore at a selected wavelength of light; and using the measured absorbance and the calibration curve for the selected wavelength of light to determine the concentration of the friction reducer in the fluid that has been recovered from the wellbore. Optionally, the method further comprising the step of preparing the calibration curve, wherein the preparation of the calibration curve comprises: preparing a plurality of reference fluid samples having a range of known concentrations of the friction reducer, treating the reference fluid samples with the reactive agent, measuring the light absorbance of each of the treated reference fluid samples, and fitting a trend-line to the light absorbance data. Optionally, the method further comprises adding a masking agent comprising sodium citrate to the sample before the reactive agent is added to the sample. Optionally, the photo-detectable compound is a precipitate. Optionally, the fluid further comprises an additive selected from the group of additives consisting of a surfactant, a proppant particle, a corrosion inhibitor, a clay stabilizer, and any combination thereof.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. While numerous changes may be made by those skilled in the art, such changes are encompassed within the spirit of the subject matter defined by the appended claims. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. In particular, every range of values (e.g., "from about a to about b," or, equivalently, "from approximately a to b," or, equivalently, "from approximately a-b") disclosed herein is to be understood as referring to the power set (the set of all subsets) of the respective range of values. The terms in the claims have their plain, ordinary meaning unless otherwise explicitly and clearly defined by the patentee.

What is claimed is:

1. A method comprising:
introducing a fluid comprising an aqueous base fluid and a friction reducer into a wellbore penetrating at least a portion of a subterranean formation at a pressure sufficient to create or enhance one or more fractures within the subterranean formation;
recovering at least a portion of the fluid from the wellbore;
adding a reactive agent comprising an ammonium chloride cationic dye to a sample of the portion of the fluid that has been recovered from the wellbore, wherein the reactive agent reacts with the friction reducer to form a photo-detectable compound in the sample;
measuring a light absorbance of the sample of the fluid that has been recovered from the wellbore at a selected wavelength of light; and
using the measured absorbance and a calibration curve for the selected wavelength of light to determine the concentration of the friction reducer in the fluid that has been recovered from the wellbore.

2. The method of claim 1 further comprising the step of preparing the calibration curve, wherein the preparation of the calibration curve comprises:
preparing a plurality of reference fluid samples having a range of known concentrations of the friction reducer,
treating the reference fluid samples with the reactive agent,
measuring the light absorbance of each of the treated reference fluid samples, and
fitting a trend-line to the light absorbance data.

3. The method of claim 1 wherein the reactive agent comprises diisobutylphenoxyethoxyethyl dimethylbenzylammonium chloride.

4. The method of claim 1 further comprising adding a masking agent comprising sodium citrate to the sample before the reactive agent is added to the sample.

5. The method of claim 1 wherein the photo-detectable compound is a precipitate.

6. The method of claim 1 wherein the friction reducer comprises polyacrylamide.

7. The method of claim 1 wherein the fluid further comprises an additive selected from the group of additives consisting of a surfactant, a proppant particle, a corrosion inhibitor, a clay stabilizer, and any combination thereof.

8. The method of claim 1 wherein the fluid is injected into the wellbore using one or more pumps.

9. A method comprising:
introducing a fluid comprising an aqueous base fluid and a friction reducer comprising polyacrylamide into a wellbore penetrating at least a portion of a subterranean formation;
recovering at least a portion of the fluid from the wellbore;
adding a reactive agent comprising diisobutylphenoxyethoxyethyl dimethylbenzylammonium chloride to a sample of the portion of the fluid that has been recovered from the wellbore, wherein the reactive agent reacts with the friction reducer to form a photo-detectable compound in the sample;
measuring a light absorbance of the sample of the fluid that has been recovered from the wellbore at a selected wavelength of light; and
using the measured absorbance and a calibration curve for the selected wavelength of light to determine the concentration of the friction reducer in the fluid that has been recovered from the wellbore.

10. The method of claim 9 further comprising the step of preparing the calibration curve, wherein the preparation of the calibration curve comprises:
preparing a plurality of reference fluid samples having a range of known concentrations of the friction reducer,
treating the reference fluid samples with the reactive agent,
measuring the light absorbance of each of the treated reference fluid samples, and
fitting a trend-line to the light absorbance data.

11. The method of claim 9 further comprising adding a masking agent comprising sodium citrate to the sample before the reactive agent is added to the sample.

12. The method of claim 9 wherein the photo-detectable compound is a precipitate.

13. The method of claim 9 wherein the fluid further comprises an additive selected from the group of additives consisting of a surfactant, a proppant particle, a corrosion inhibitor, a clay stabilizer, and any combination thereof.

14. The method of claim 9 wherein the fluid is injected using one or more pumps.

15. The method of claim 14 wherein the fluid is injected into the wellbore at a pressure sufficient to create or enhance one or more fractures within the subterranean formation.

16. A method comprising:
introducing a fluid comprising an aqueous base fluid and a friction reducer comprising polyacrylamide into a wellbore penetrating at least a portion of a subterranean formation at a pressure sufficient to create or enhance one or more fractures within the subterranean formation;
recovering at least a portion of the fluid from the wellbore;
adding a reactive agent comprising diisobutylphenoxyethoxyethyl dimethylbenzylammonium chloride solution to a sample of the portion of the fluid that has been recovered from the wellbore, wherein the reactive agent reacts with the friction reducer to form a photo-detectable compound in the sample;
measuring a light absorbance of the sample of the fluid that has been recovered from the wellbore at a selected wavelength of light; and
using the measured absorbance and the calibration curve for the selected wavelength of light to determine the concentration of the friction reducer in the fluid that has been recovered from the wellbore.

17. The method of claim 16 further comprising the step of preparing the calibration curve, wherein the preparation of the calibration curve comprises:
preparing a plurality of reference fluid samples having a range of known concentrations of the friction reducer,
treating the reference fluid samples with the reactive agent,
measuring the light absorbance of each of the treated reference fluid samples, and
fitting a trend-line to the light absorbance data.

18. The method of claim 16 further comprising adding a masking agent comprising sodium citrate to the sample before the reactive agent is added to the sample.

19. The method of claim 16 wherein the photo-detectable compound is a precipitate.

20. The method of claim 16 wherein the fluid further comprises an additive selected from the group of additives consisting of a surfactant, a proppant particle, a corrosion inhibitor, a clay stabilizer, and any combination thereof.

* * * * *